US007384410B2

(12) United States Patent
Eggers et al.

(10) Patent No.: US 7,384,410 B2
(45) Date of Patent: Jun. 10, 2008

(54) SYSTEM AND METHOD FOR MANAGING PATIENT CARE

(75) Inventors: Philip N. Eggers, Poway, CA (US); David L. Schlotterbeck, Laguna Niguel, CA (US); Timothy W Vanderveen, Poway, CA (US); Damon J. Coffman, San Diego, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 1452 days.

(21) Appl. No.: 09/793,475

(22) Filed: Feb. 26, 2001

(65) Prior Publication Data
US 2002/0169636 A1 Nov. 14, 2002

Related U.S. Application Data

(63) Continuation-in-part of application No. 09/379,212, filed on Aug. 23, 1999, now Pat. No. 7,074,205, which is a continuation of application No. 08/871,307, filed on Jun. 9, 1997, now Pat. No. 5,941,846, which is a continuation-in-part of application No. 08/403,503, filed on Mar. 13, 1995, now Pat. No. 5,713,856.

(51) Int. Cl.
*A61M 31/00* (2006.01)
(52) U.S. Cl. ........................................................ 604/67
(58) Field of Classification Search ............. 604/30–34, 604/65, 66, 67, 49, 50, 53, 118, 151, 246; 128/DIG. 12, DIG. 13; 606/39, 42
See application file for complete search history.

(56) References Cited

U.S. PATENT DOCUMENTS

| 4,785,969 A | 11/1988 | McLaughlin |
| 4,847,764 A | 7/1989 | Halvorson |
| 4,857,713 A | 8/1989 | Brown |
| 5,038,800 A | 8/1991 | Oba |
| 5,041,086 A | 8/1991 | Koenig et al. |
| 5,047,948 A | 9/1991 | Turner |
| 5,153,827 A | 10/1992 | Coutre et al. |
| 5,301,105 A | 4/1994 | Cummings, Jr. |
| 5,317,506 A | 5/1994 | Coutre et al. |

(Continued)

FOREIGN PATENT DOCUMENTS

JP  2000189514 A  6/1999

*Primary Examiner*—Manuel Mendez
(74) *Attorney, Agent, or Firm*—Fulwider Patton LLP

(57) ABSTRACT

The present invention is directed to a system and method for providing care to a patient, comprising a patient care device having a number of configuration databases stored in a memory in the device. Each configuration database preferably includes protocols, operating limits, rule sets and/or operating features that collectively define an operating environment, or personality, of the device. Selection of a specific configuration database preferably is based at least in part upon patient-specific information obtained from any location in a distributed hospital network. Examples of such patient-specific information include patient age or size, patient medical characteristics, a location of the patient or a location of the care device. In a preferred embodiment, programming a patient care device to deliver a drug to a patient entails activating a configuration database and scanning a machine-readable drug label identifying a particular protocol stored in the activated database. The selected protocol includes default parameters for delivering the drug, and the label optionally includes instructions for deviating from the default protocol.

18 Claims, 7 Drawing Sheets

U.S. PATENT DOCUMENTS

| | | |
|---|---|---|
| 5,573,506 A | 11/1996 | Vasko |
| 5,640,953 A | 6/1997 | Bishop et al. |
| 5,713,856 A * | 2/1998 | Eggers et al. ................. 604/65 |
| 5,732,401 A | 3/1998 | Conway |
| 5,781,442 A | 7/1998 | Engleson et al. |
| 5,871,465 A | 2/1999 | Vasko |
| 5,885,245 A | 3/1999 | Lynch et al. |
| 5,890,129 A | 3/1999 | Spurgeon |
| 5,895,371 A | 4/1999 | Levitas et al. |
| 5,924,074 A | 7/1999 | Evans |
| 5,941,846 A | 8/1999 | Duffy et al. |
| 5,963,565 A | 10/1999 | Rezvani et al. |
| 6,055,458 A | 4/2000 | Cochran et al. |
| 2002/0026330 A1 | 2/2002 | Klein |

* cited by examiner

SYSTEM AND METHOD FOR MANAGING PATIENT CARE

RELATED APPLICATIONS

This application is a continuation-in-part of application Ser. No. 09/379,212, filed Aug. 23, 1999; now U.S. Pat. No. 7,074,205, issued Jul. 11, 2006; which is a continuation of application Ser. No. 08/871,307, filed Jun. 9, 1997, now U.S. Pat. No. 5,941,846, issued Aug. 24, 1999; which is a continuation-in-part of application Ser. No. 08/403,503, filed Mar. 13, 1995, now U.S. Pat. No. 5,713,856, issued Mar. 3, 1998. These related patents/applications are herein incorporated by reference in their entireties.

TECHNICAL FIELD

The present invention relates generally to a system and method for managing patient care in a heath care facility, and in particular to a system and method for integrating information from a distributed network to alter the operating characteristics of a patient care device.

BACKGROUND OF THE INVENTION

Much attention in the health care industry has been placed on reducing the incidence of medication dosing errors and improving overall quality of patient care. Often medication dosing errors occur because a patient receives the wrong medication, a wrong dosage of the correct medication, the correct dosage of the correct medication at the wrong time, or the medication has harmful interaction with other drugs. Recent advances in the health care field have attempted to address these problems and to enhance efficiency and quality of patient care.

Many drugs are dispensed for patient use at or close to the point of care using programmable infusion pumps such as those disclosed by U.S. Pat. No. 5,713,856 to Eggers et al. and U.S. Pat. No. 5,041,086 to Koenig et al., both of which are incorporated herein by reference. Eggers et al. discloses a modular patient care system capable of providing therapy to a patient and monitoring patient condition. The system of Eggers utilizes a central control module to control and monitor a number of functional modules, including one or more infusion pumps and patient monitoring devices.

Most hospitals today have a pharmacy equipped with a computerized system for entering, preparing, and tracking prescriptions, managing drug inventory, checking for drug incompatibilities, and printing prescription orders and labels. Typically, one or more medication infusions to be administered to a patient are prescribed by the patient's physician. The pharmacy prepares the infusion solution according to the physician's prescription and places the solution in an IV bag, syringe or other container. A printed label identifying the container contents, the patient to whom the medication is prescribed, the prescribing physician, delivery instructions and/or other information regarding the prescription. The label is generally typed or printed in human readable characters. In some instances, bar codes are used to encode information on the label.

After a label is affixed, the container is transported to the patient's location and operatively attached to a bedside infusion pump system, such as that disclosed by Eggers et al. A nurse or other care provider then programs the infusion system with drug delivery data from the label, typically by manually entering infusion parameters using a keyboard or a keypad. Alternatively, some systems seek to reduce data entry errors by incorporating a bar code reader that scans coded data into the pump system from the drug label or from a prescription order. The data may include, for example, rate of infusion, total volume to be infused (VTBI) and, in multi-channel or modular systems such as that described by Eggers et al., which channel or pump module is to be used.

U.S. Pat. No. 5,153,827 to Coutré et al. discloses a system for providing an infusion apparatus with medication infusion parameters from a central pharmacy database. Infusion delivery parameters for a particular treatment are printed from the central pharmacy database on a machine-readable labels, which are then carried to the patient location and scanned into the bedside infusion apparatus. The system of Coutré requires that all information used to program a pump is either scanned from a machine-readable label or entered manually by the user. Thus, the infusion systems of Coutré do not utilize information from other sources within the hospital or within the system itself.

U.S. Pat. No. 5,781,442 to Engleson et al. discloses a patient care management system comprised of a network of computers having a variety of input and output devices for receiving patient data and for generating or displaying reports. The disclosed system monitors ongoing administrations of care to patients and automatically updates records and provides alarms when necessary. In an example of use, patient and drug identification information are scanned into a bedside terminal and communicated to a central computer, where the data are processed. The central computer then sends operating parameters to the terminal and the terminal programs an infusion pump in accordance with the operating parameters.

In spite of recent advances in the art, there remains a need in the art for a system that facilitates efficient and accurate programming of a medical treatment device while ensuring that the prescribed treatment conforms with institutional and departmental guidelines with respect to a patient in a particular location and/or with particular characteristics.

SUMMARY OF THE INVENTION

The present invention generally involves the movement of patient information from a variety of sources such that the patient receives a better quality of care, the care providers' assets are utilized more efficiently and labor costs are reduced through the automation of some processes now done manually. The means of data transfer is typically done within a network, or network of networks, with some data entering and exiting through portals which convert data formats. A preferred embodiment of the present invention is a modular patient care device connected to a hospital network, wherein the capabilities and operating characteristics of the device are altered as a function of its location within the network.

According to the invention there is provided a patient care system, comprising a patient care device and means for transferring patient-specific information to the device. The device includes a memory for storing a plurality of configuration databases, each of which comprises a plurality of distinct groups of device operating parameters. Transferring patient-specific information to the device enables selection of a specific configuration database from the plurality of configuration databases, based at least in part on the patient-specific information. The patient care system of the present invention also preferably includes a computer network and means for communicating between the device and the network.

Still further according to the invention there is provided a method of programming a patient care device to deliver a substance to a patient, comprising printing a coded label, said label including a protocol pointer identifying a first protocol for delivering the substance to the patient; attaching the label to a container holding the substance; transporting the container to the patient care device; entering the pointer into the patient care system, the patient care system including the first protocol in a memory; and programming a functional unit of the patient care system to deliver the substance to the patient in accordance with the first protocol.

BRIEF DESCRIPTION OF THE DRAWINGS

For a better understanding of the nature and details of the invention, reference should be made to the following detailed description taken in conjunction with the accompanying drawings, in which.

Like reference numerals refer to corresponding parts throughout the several views of the drawings.

DESCRIPTION OF THE INVENTION

Figure 1:
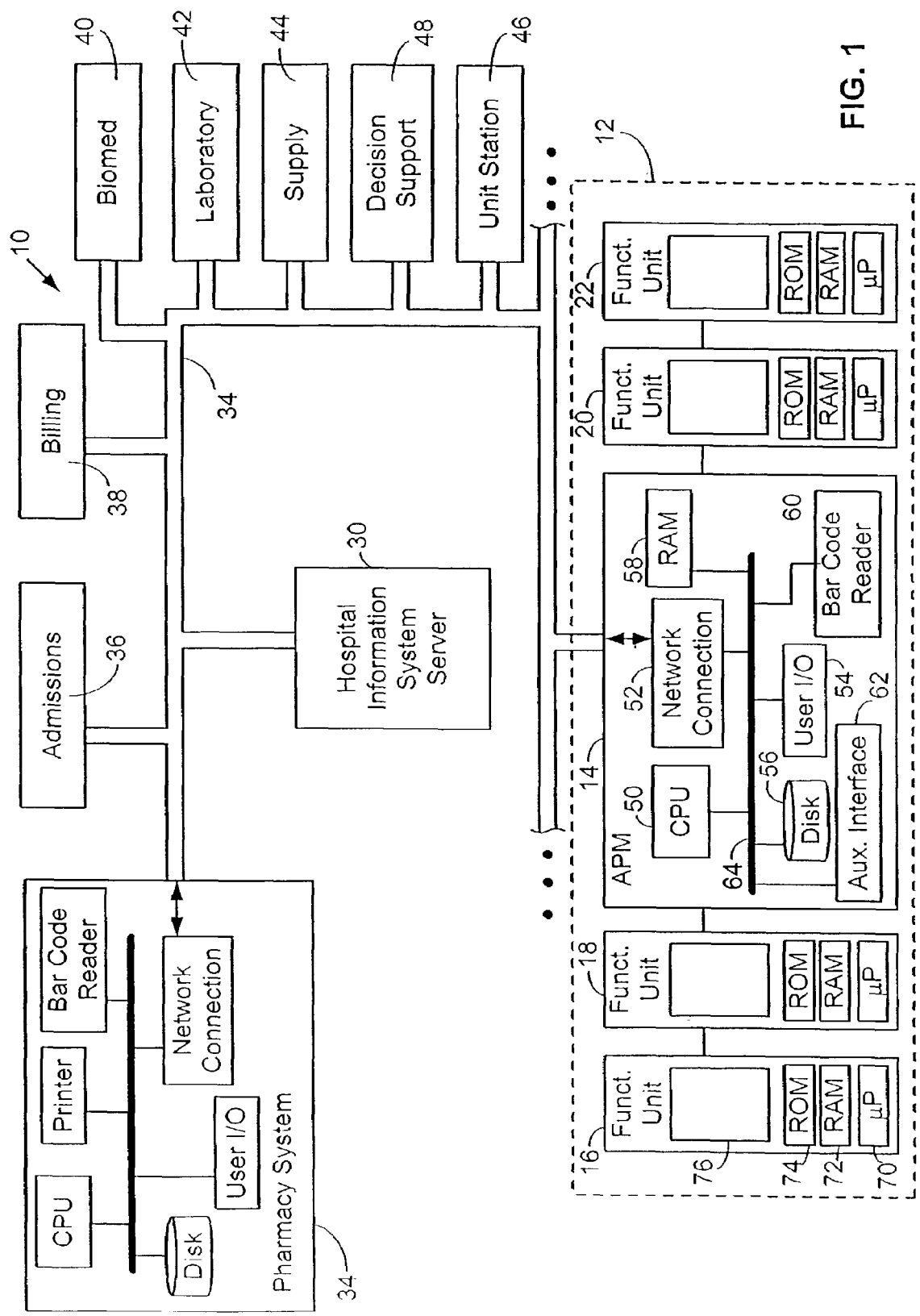
FIG. 1 is a schematic diagram of a patient care management system according to the present invention.

FIG. 1 is a general illustration of a patient care system in accordance with one embodiment of the present invention. In FIG. 1, a patient care device 12 is connected to a hospital network 10 including a pharmacy management system 34 and a hospital information system server 30. Each element 12, 30 and 34 is connected to network 10 by a transmission channel 32. Transmission channel 32 is any wired or wireless transmission channel, for example a 802.11 wireless local area network (LAN). In a preferred embodiment of the present invention, network 10 also includes computer systems located in various departments throughout a hospital. For example, network 10 of FIG. 1 optionally includes computer systems associated with an admissions department 36, a billing department 38, a biomedical engineering department 40, a clinical laboratory 42, a central supply department 44, one or more unit station computers and/or a medical decision support system 48.

Patient care device 12 preferably comprises a system similar to that described in U.S. Pat. No. 5,713,856 to Eggers et al., which is incorporated herein by reference. Alternatively, other patient care devices, such as pumps, physiological monitors (e.g., heart rate, blood pressure, ECG, EEG, pulse oximeter, and other patient monitors), therapy devices, and other drug delivery devices may be utilized according to the teachings set forth herein. Patient care device 12 preferably comprises an advanced programming module 14, also referred to as interface unit 14, connected to one or more functional modules 16, 18, 20, 22. Interface unit 14 includes a central processing unit (CPU) 50 connected to a memory, e.g. random access memory (RAM) 58, and one or more interface devices such as user interface device 54, a coded data input device 60, a network connection 52, and an auxiliary interface 62 for communicating with additional modules or devices. Interface unit 14 also preferably, although not necessarily, includes a main non-volatile storage unit 56, preferably a hard disk drive, for storing software and data and one or more internal buses 64 for interconnecting the aforementioned elements.

In a typical embodiment, user interface device 54 is a touch screen for displaying information to a user and allowing a user to input information by touching defined areas of the screen. Alternatively, user interface device 54 could include any means for displaying and inputting information, such as a monitor, a printer, a keyboard, softkeys, a mouse, a track ball and/or a light pen. Coded data input device 60 is preferably a bar code reader capable of scanning and interpreting data printed in bar coded format. Alternatively, data input device 60 could be any device for entering coded data into a computer, such as devices for reading a magnetic strips, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and coded data input device 60 may be the same device. Alternatively, although data input device 60 is shown in FIG. 1 to be disposed within interface unit 14, one skilled in the art will recognize that data input device 60 may be integral within pharmacy system 34 or located externally and communicating with pharmacy system 34 through an RS-232 serial interface or any other appropriate communication means. Auxiliary interface 62 is preferably an RS-232 communications interface, however any other means for communicating with a peripheral device such as a printer, patient monitor, infusion pump or other medical device may be used without departing from the scope of the invention.

Network connection 52 is preferably a direct network connection such as a T1 connection, an integrated services digital network (ISDN) connection, a digital subscriber line (DSL) modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection.

Functional modules 16, 18, 20, 22 are any devices for providing care to a patient or for monitoring patient condition. In preferred embodiment of the present invention, at least one of functional modules 16, 18, 20, 22 is an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor. Alternatively, functional module 18, 20 and/or 22 may be a printer, scanner or any other peripheral input/output device.

Each functional module 16, 18, 20, 22 communicates directly or indirectly with interface unit 14, with interface unit 14 providing overall monitoring and control of device 12. In a preferred embodiment, functional modules 16, 18, 20, 22 are connected physically and electronically in serial fashion to one or both ends of interface unit 14 as shown in FIG. 1 and as detailed in Eggers et al. However, one skilled in the art will recognize that there are other means for connecting functional modules with the interface unit may be utilized without departing from the scope of the invention. It will also be appreciated that devices such as pumps or monitors that provide sufficient programmability and connectivity may communicate directly with the network without a separate interface unit. As described above, additional medical devices or peripheral devices may be connected to patient care device 12 through one or more auxiliary interfaces 62.

Each functional module 16, 18, 20, 22 typically includes module-specific components 76, a microprocessor 70, a volatile memory 72 and a non-volatile memory 74 for storing information. It should be noted that while four functional modules are shown in FIG. 1, any number of devices may be connected directly or indirectly to central computer 14. The number and type of functional modules described herein are intended to be illustrative, and in no way limit the scope of the present invention. Module-specific components 76 include any components necessary for operation of a particular module, such as a pumping mechanism for infusion pump module 16.

While each functional module is typically capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

In a preferred embodiment of the present invention, patient care device 12 is capable of operating in several different modes, or personalities, with each personality defined by a configuration database. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, e.g. from pharmacy 34, admissions 36, laboratory 42, etc.

Data to and from the various data sources can be converted into network-compatible data with existing technology, and movement of the information between the medical device and network can be accomplished by a variety of means. For example, patient care device 12 and network 10 may communicate via automated interaction and/or manual interaction. Automated interaction may be continuous or intermittent and may occur through direct network connection 54 (as shown in FIG. 1), or alternatively through RS232 links, MIB systems, RF links such as BLUETOOTH (Amtel Corp., San Jose, Calif.), IR links, WLANS, digital cable systems, telephone modems or other communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. Preferably, the communication means is bidirectional with access to data from as many points of the distributed data sources as possible. Decision-making can occur at a variety of places within network 10. For example, and not by way of limitation, decisions can be made in HIS server 30, decision support 48, hospital department or unit stations 46, or within patient care device 12 itself.

Figure 2:
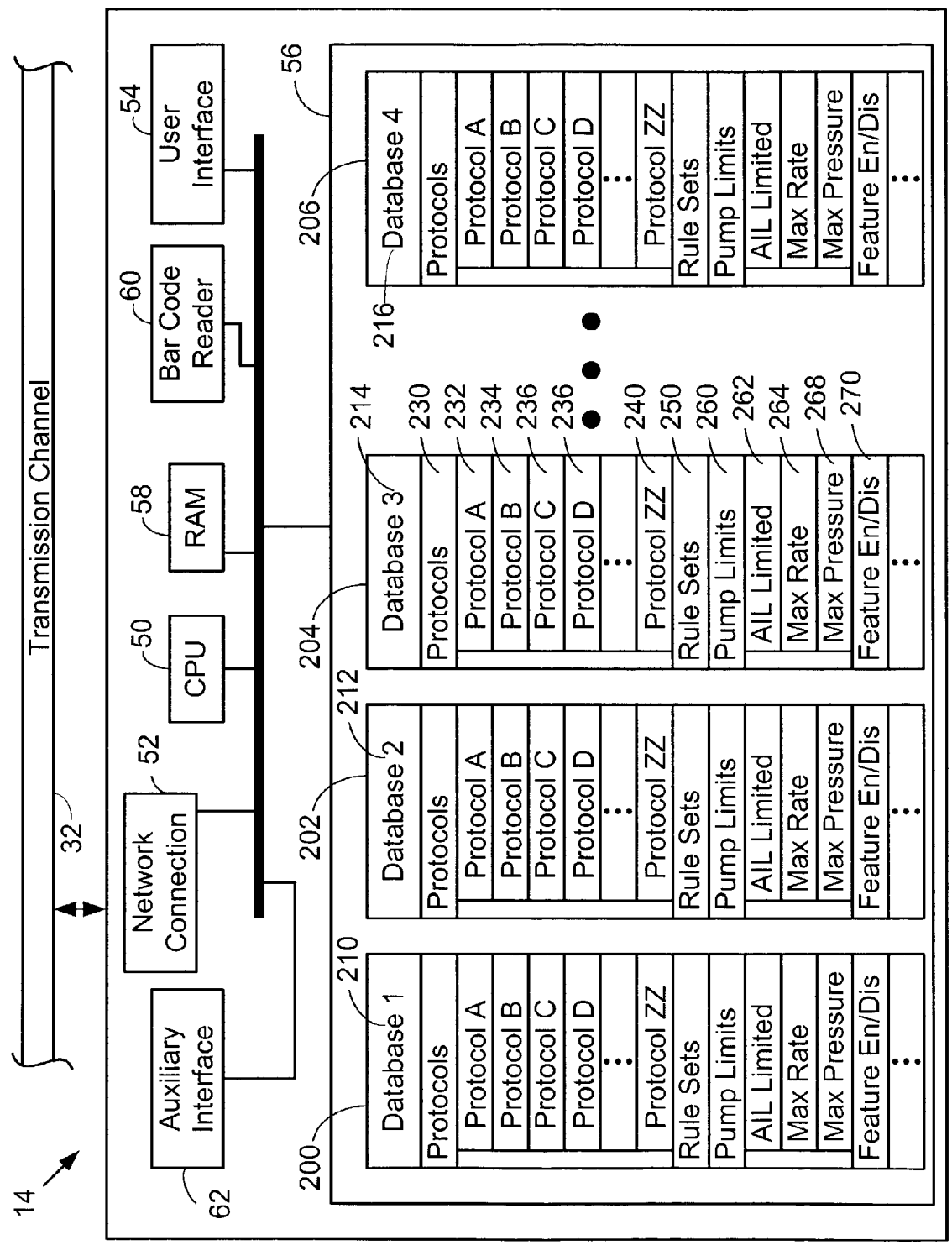
FIG. 2 is a schematic diagram of an interface unit according to the present invention.

Referring to FIG. 2, in a preferred embodiment of the present invention, interface unit 14 of patient care device 12 includes a plurality of configuration databases 200, 202, 204 and 206. The configuration databases are preferably stored in memory 56 of interface unit 14, however one or more databases may be stored within a functional module 16, 18, 20, 22. One skilled in the art will understand that, while memory 56 is preferably an internal hard disk, any permanent or removable storage media including, but not limited to, CD-ROM, EEPROM, diskette, tape, external hard disk, memory card, flash memory, etc. may be used. Optionally, portions of configuration databases 200, 202, 204, 206 may be stored in volatile memory such as RAM 58.

Each configuration database 200, 202, 204, 206 preferably includes a unique database identifier, or pointer, 210, 212, 214, 216, for identifying the respective database. Each database 200, 202, 204, 206 includes a plurality of fields which define, for example, available treatment protocols, drug library information, module operating limits, rule sets, device features and possibly other information for defining a particular operating parameters for patient care device 12. Each configuration database 200, 202, 204, 206 defines a specific operating environment, or personality, for patient care device 12. The individual configuration databases may be treatment location specific (e.g. intensive care unit [ICU], neonatal intensive care unit [NICU], pediatrics, oncology, etc.), disease state specific (intracranial pressure management, bone marrow transplant, etc.), user specific (LPN, RN, physician, etc.), or created by any other rationale. For example, according to one embodiment of the present invention, when patient care device 12 is located in the ICU it utilizes configuration database 200, and when device 12 is located the NICU it utilizes configuration database 202. Each database 200 and 202, respectively, contains particular operating parameters, treatment protocols, features etc. that configure device 12 for use with patients in that unit of the hospital.

It should be noted that while FIG. 2 shows that each database includes the same categories and types of information, the databases may vary considerably in terms of the types and amounts of information they contain. Each of the various configuration databases, when selected, at least in part defines the operating environment of device 12 and includes a number of protocols or groups of default operating parameters.

Figure 3:
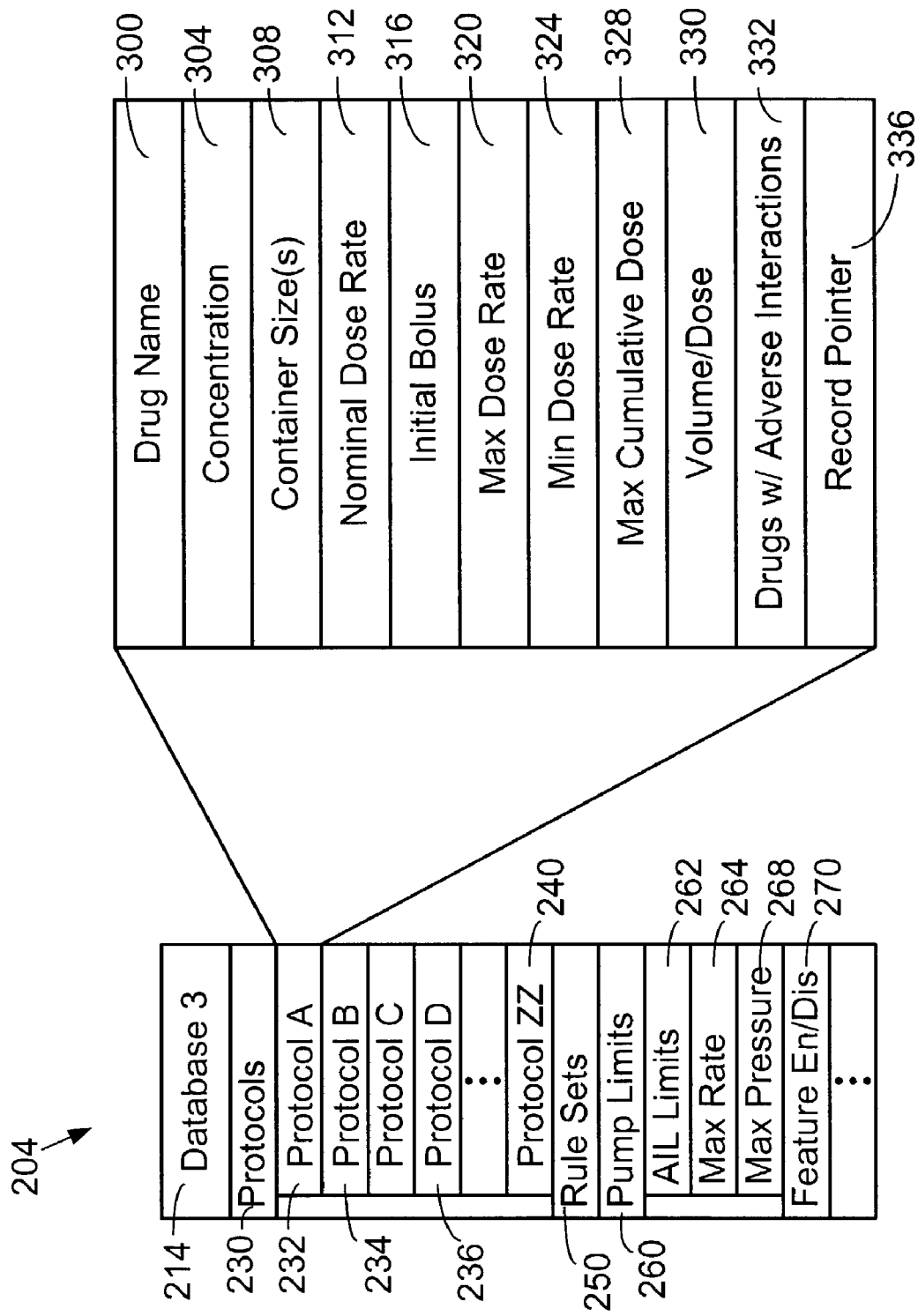
FIG. 3 is a schematic diagram illustrating a configuration database according to the present invention.

FIG. 3 is a more detailed representation of a sample configuration database 204 according to the present invention. Configuration database 204 includes a protocol module 230 comprising a plurality of protocols 232, 234, 236, 238, 240. Each protocol includes a plurality of fields of default operating parameters. In some cases an infusion protocol may include a complete detailed infusion instruction with all of the default parameter values defined. Other infusion protocols may have partially defined parameters with additional data entry required by the user at the point of care. For example, protocol A 232 of FIG. 3 includes fields of default operating parameter values and other data for controlling a medication infusion pump. The fields of this example include drug name 300, concentration 304, container size(s) 308, nominal dose rate 312, initial bolus 316, maximum dose rate 320, minimum dose rate 324, maximum cumulative dose 328, drug incompatibility 332 and an ID field, record pointer 336, for identifying or "calling" the protocol record. Each field typically includes stored default parameter values that collectively define a specific infusion protocol. Some fields, such as Drug Incompatibility 332, include a reference or link to another database or drug library containing relevant information.

Such references to commonly used data libraries allow data to be shared between protocols and/or configuration databases to avoid duplicate storage and entry and to allow efficient updating of database information. Similarly, all protocols need not be stored within each configuration database. Rather, protocols from different configuration databases may be saved in a master database or library, with each individual configuration database containing reference links to particular protocols stored in the library. Such an arrangement is advantageous because it avoids duplicate storage of identical protocols and facilitates updating of library information.

When such a protocol is selected certain information must be provided. For example, device 12 may query the network to automatically obtain data such as patient weight from the patient's electronic records in admissions 36, critical dosage parameters from pharmacy system 34 and double check with laboratory 42 for recent test results which may contraindicate the prescribed medication. A double check with pharmacy system 34 of information coded on the drug prescription label also may be automatically performed. Alternatively, the user may enter data such as the patient weight and total dosage directly into the device. and confirms the automatically selected parameters. In one embodiment of the invention, information in a drug specific protocol is a superset of the information in the "drug library". Consequently, if the user selects a drug name, then certain parameters in the record are applied. Such parameters would typically include the drug name, delivery rate limits, units of delivery, possibly concentration and container size. The user would enter or scan in missing data such as patient weight, drug amount, diluent volume, dosage rate, total dosage and confirm the automatically selected parameters as prompted.

Different protocols typically include different fields and/or different parameter values. Thus, Protocol B 234 might include additional fields compared to Protocol A 232, where the additional fields define instructions and/or parameters for implementing one or more different infusion types such as primary/secondary infusion, multichannel coordinated infusion and multidose protocols (see FIG. 4). Alternatively, Protocol B 234 could include the same fields as Protocol A 232, and differ only in terms of one or more parameter values in one of the fields. For example, both protocols could be for infusion of the drug dopamine, where one protocol has a concentration 304 value of 400 mg/250 mL while the other has a concentration 304 value of 800 mg/mL.

Referring again to FIG. 3, the Rule Sets module 250 of database 204 includes rules and/or algorithms that may be used to help define particular parameters within a database. For example, Rule Sets module 250 could include an algorithm that modifies the maximum allowable infusion rate or some other parameter based upon data obtained from other sources in network 10, such as patient age, body weight or medical history from Admissions 36 or test results from Laboratory 42. Other rule sets in the Rule Sets module 250 may provide warnings or recommendations upon the occurrence of particular events within pump module 16, such as occlusion of the infusion line.

Still other rule sets within module 250 may contain algorithms that utilize measurements from one or more functional modules to modify operation of another functional module. For example, module 250 may contain a rule set that monitors blood pressure and intracranial pressure in a head trauma patient and calculates resulting perfusion pressure. The system then notifies the user when perfusion pressure falls outside of a defined range and recommends adjusting infusion rate of a therapeutic agent to increase blood pressure or to decrease intracranial pressure.

The Pump Limits module 260 of database 204 contains information that defines the overall operating limits of infusion pump module 16 and other pump devices, if any, attached to interface unit 14. The Pump Limits module 260 typically includes at least three fields, Air In Line (AIL) Limits 262, Max Rate 264, and Max Pressure 268. Because the Pump Limits module 260 of each configuration database 200, 202, 204, 206 potentially contains different parameters and values, module 260 helps define the operating characteristics or mode in which device 14 operates when a particular configuration database 200, 202, 204, 206 is active.

AIL Limits 262 defines an allowable limit for the amount of air in an infusion line connected to a patient. Allowable AIL Limits may differ for particular patients or particular locations in the hospital. For example, an allowable limit of 50 μL may be set for pediatric patients, while a limit of 100-200 μL is used for general adult patients and 500 μL for operating room and/or trauma patients.

Max Rate 264 defines the maximum allowable infusion rate for an infusion pump operating under that particular configuration database 20. Again, the defined Max Rate 264 values may differ among patient class, attributes, location, etc. For example, the maximum rate for delivering heparin to pediatric patients may be set at 10 units/Kg/hr, while adult patients have a limit of 500-1000 units/hr.

Figure 4:
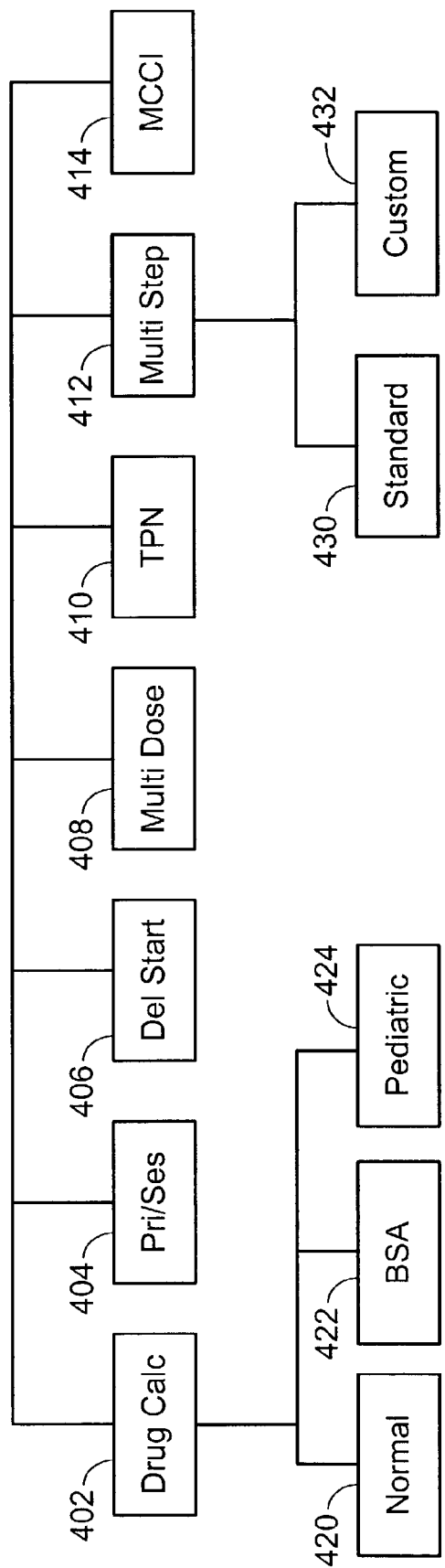
FIG. 4 is a block diagram illustrating a number of different infusion types supported by the interface unit of the present invention.

Feature Enable/Disable module 270 of configuration database 204 defines which particular infusion types, or features, are available to the user of system 14 when configuration database 204 is activated. In a preferred embodiment of the present invention, patient care system 14 is capable of supporting a wide variety of such features, ranging from simple primary infusions used for hydration and keep-vein-open (KVO) applications to complex multichannel delivery applications. FIG. 4 illustrates some of the various features or infusion types that are supported by patient care system 14 according to one embodiment of the present invention. These features include, but are not limited to, Drug Calc 402, Primary/Secondary 404, Delayed Start (Del Start) 406, Multi Dose 408, Total Parenteral Nutrition (TPN) 410, Multi Step 412, and Multi-Channel Coordinated Infusion (MCCI) 414. As mentioned previously, each of these features or infusion types may be implemented by a particular protocol stored in protocols module 230. The foregoing features are described briefly below; see U.S. Pat. No. 5,713,856 for a more detailed description of each.

Drug Calc 402 is a feature that allows calculation of drug infusion parameters such as rate or dose, based on patient weight, time units, and drug concentration. For example, the drug calculation function of the system allows the user to either: enter the desired drug dose and the infusion pump functional unit microprocessor calculates the correct flow rate to achieve the desired dose; enter the desired flow rate and the pump functional unit calculates the corresponding drug dose; or enter the desired bolus dose and the duration and the pump functional unit calculates the bolus rate and the VTBI. The system may additionally include a pediatric drug calculation function 424 which allows the user to enter, for example, flow rate, dose, and diluent volume. From these user entered parameters, the system calculates the amount of drug to admix with the diluent to achieve a drug concentration consistent with the selected dose and flow rate. Additional details regarding Drug Calc 402 features are found in U.S. Pat. No. 5,713,856.

Typically, Drug Calc 402 mode is used to ensure accuracy of infusion rate data where a user enters at least a portion of the infusion program data manually, e.g. through a touch screen or a keypad. For example, Drug Calc 402 may be used in conjunction with a drug-specific protocol such as stored in a configuration database. Alternatively, Drug Calc 402 feature may be used in combination with a stored protocol that is identified by a coded label to calculate missing parameter values or to recalculate new values (e.g. when a prescription includes a deviation from the standard protocol values).

Pri/Sec 404 feature allows use of protocols utilizing a primary infusion in conjunction with a secondary infusion solution. Historically a primary infusion with an antibiotic secondary would be programmed by entering the primary and secondary rate and VTBI. In the present invention, a user can simply select the appropriate antibiotic regimen from the list infusion protocols and have the appropriate parameters automatically retrieved. The user may then simply confirm the parameters and start the infusion.

Delay Start 406 delays the start of an infusion protocol or other treatment for a particular duration of time or until a particular time of day. Alternatively, start may be delayed until the happening of a particular event. Such events include, but are not limited to, a signal from the interface unit in response to measured vital signs or other physiological parameters, completion of a stage of treatment by another module, or a signal or data received by system 14 over network 10.

Multi Dose 408 allows multiple doses of a drug to be delivered over time. A protocol incorporating the Multi Dose 408 feature typically includes parameters for infusion rate, volume/dose, dose interval, number of doses and start time. As with all other protocols stored in a configuration database, a stored Multi Dose 408 protocol may be selected or activated from the configuration database simply by scanning a coded drug label containing the protocol identifier (with or without instructions for deviating from the default protocol values). Any missing or different values may then be entered by the user.

TPN 410 provides for total perenteral nutrition delivery using standard or custom ramp and taper protocols known to those skilled in the art. For example, a typical TPN protocol for delivering 2500 calories over an eight hour period utilizes an initial slow rate of delivery with a gradual increase to a maintenance rate for a period of six to seven hours, then a gradual decrease to complete the infusion.

Multi Step 412 is similar to TPN 410 in that it allows delivery of a substance at various rates/volumes during a protocol. Standard 430 defines standard multi-step protocols that are commonly used without deviation for different patients. Custom 432 defines multi-step delivery protocols that are customized for particular situations. For example, a custom multi-step protocol may be used for delivery of dobutamine to increase heart rate during a stress test. Such a protocol typically varies the delivery profile of the drug to a patient over time, and patient weight or age is used as a factor to select a particular profile. Any number of custom multi-step protocols may be defined and used by one skilled in the art.

Figure 5:
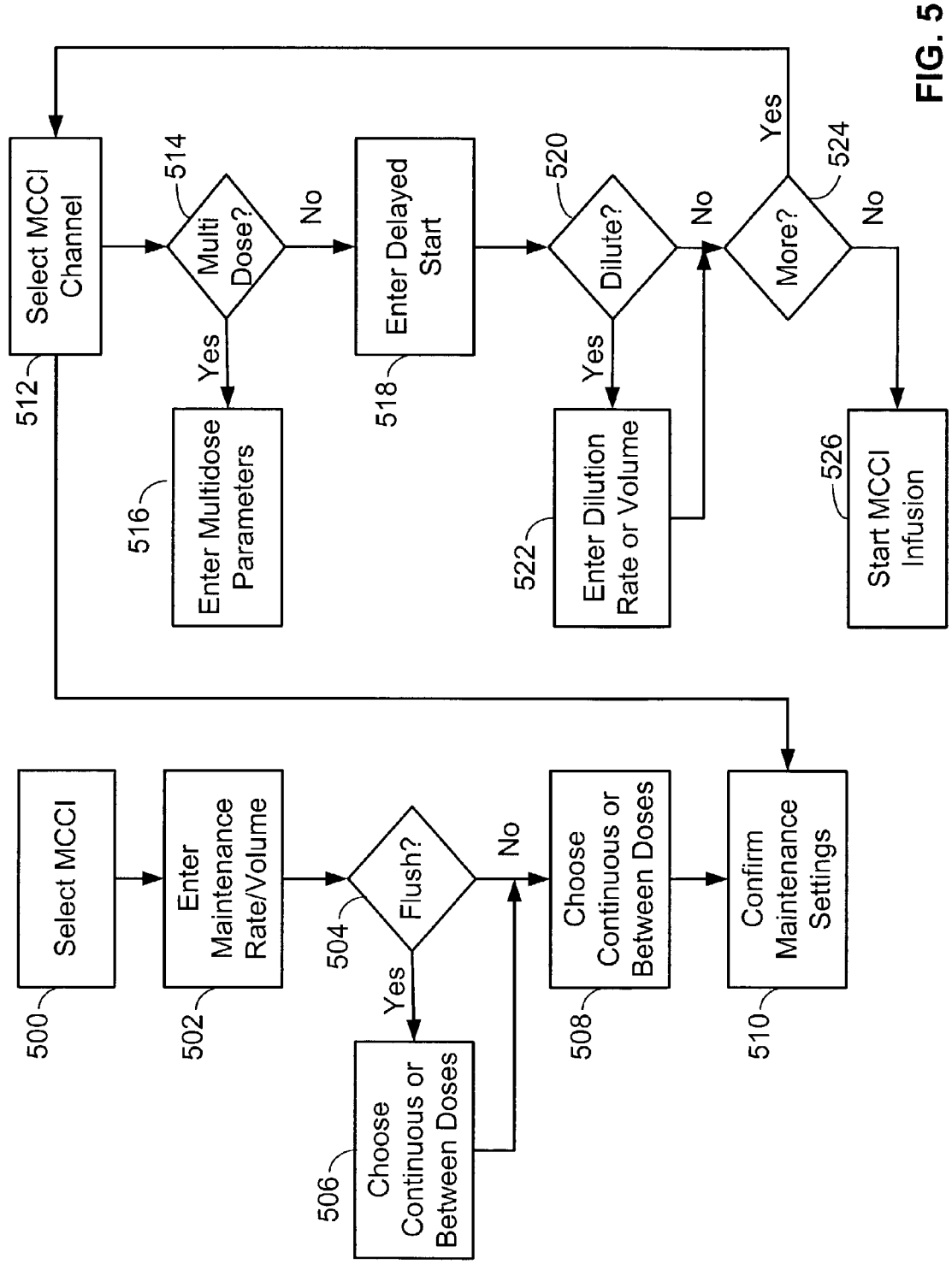
FIG. 5 illustrates the process steps for programming an infusion system to perform a particular infusion protocol in accordance with one embodiment of the present invention.

MCCI 414 may be used in conjunction with Multi Dose 408 and/or Delay Start 406 features to program complex coordinated infusion involving different solutions being infused from multiple modules, or channels. FIG. 5 illustrates a process flow for manually setting up a typical multichannel coordinated infusion according to the present invention. After the MCCI 414 function is selected in step 500 from a menu of operations displayed by the interface unit, the user is prompted to enter maintenance rate/volume 502. The user is then queried as to whether a flush 504 is desired. If yes, the user is prompted to enter flush volume and duration in step 506 before going to step 508. If no flush, or after flush volume and duration are entered, the user is prompted to choose continuous or between doses 508. The user is then prompted to confirm the maintenance settings 510. The user then selects a channel to use for the coordinated infusion in step 512. Step 514 queries the user as to whether a multi-dose infusion is desired. If multi-dose is to be used for that channel, the user enters the multidose parameters in step 516; if multi-dose is not to be used, the user is prompted to enter delayed start time in step 518. If a dilution 520 will be used, the user is prompted to enter dilution rate or volume 522. After all parameters have been entered for that channel, the user is queried in step 524 as to whether additional infusions/channels are to be used. If so, steps 512-520 are repeated until all channels are configured. Once all channels are configured, the user is prompted to start the MCCI 526.

According to a preferred embodiment of the present invention, some or all of the process steps shown in FIG. 5 and the values to be entered may be defined by a protocol stored in a configuration database. In such a case, the steps of FIG. 5 may be replaced by simply scanning a coded label including the protocol identification, or alternatively by selecting the desired protocol from a menu, and verifying the parameter values.

One skilled in the art will appreciate that the features and infusion types shown in FIG. 4 is intended to be illustrative of the present invention, and that patient care device 14 may support additional or different features than those described herein.

Figure 6:
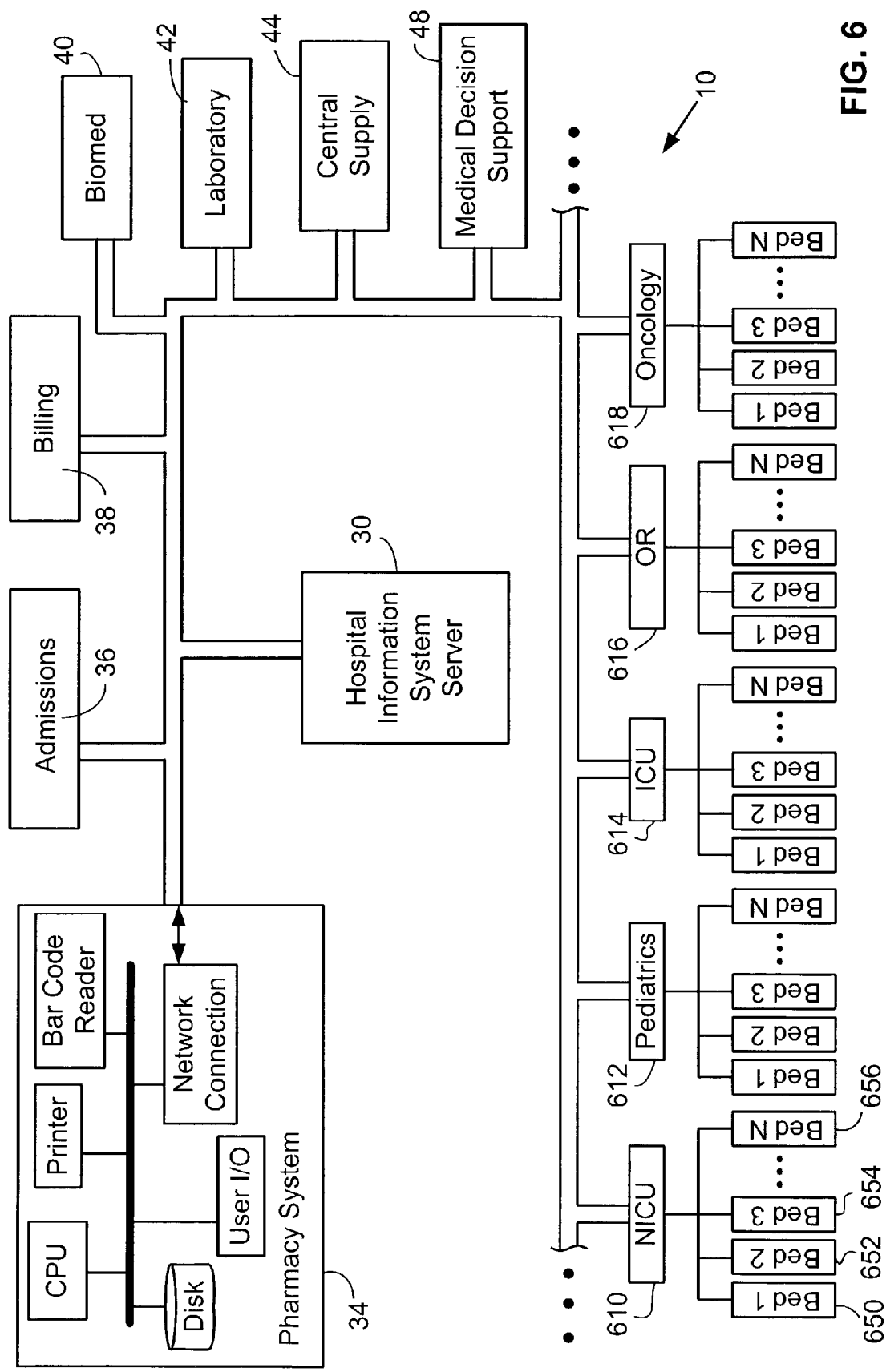
FIG. 6 is a schematic diagram of an alternative embodiment of the patient care management system of the present invention.

In a preferred embodiment of the present invention, a plurality of patient care systems 12 are linked through a local area network (LAN) to a floor or unit server as shown in FIG. 6. For example, in a neonatal intensive care unit (NICU) having an NICU server 610, a plurality of bedside patient care devices 650, 652, 654 and 656 are connected through a LAN 620 to unit server 610. Similar network servers may be provided throughout the hospital, such as pediatrics 612, intensive care unit (ICU) 614, surgery (OR) 616 and oncology 618. Unit server 610 may contain the configuration database information for that particular unit. The configuration databases in patient care device 12 could be updated periodically by downloading them from the unit server. Alternatively, a particular configuration database could be downloaded from the server as it is selected for use in patient care system 650, 652, 654 or 656. Still another alternative is to have a unit- or department-specific configuration database that is automatically downloaded into a patient care system 650, 652, 654, 656 when the system is operatively connected to the department LAN. In any case, having some or all of the configuration database information stored in the unit server 610, 612, 614, 616, 618 facilitates management and updating of the databases. U.S. Pat. No. 5,718,442 to Engleson et al., which is incorporated herein by reference, describes a system for connecting bedside medical devices to a hospital network, or network of networks, that may be suitable for use with the present invention.

In yet another an alternative embodiment of the present invention, patient care device 12 is not directly connected to network 10. Rather, information is indirectly connected to network 10 using data input device 60, user interface 54, auxiliary interface 62 or other communication means. Such communication means include, but are not limited to, RS232 links, MIB systems, IR links, WLANS, portable data assistants, memory cards, portable storage media or any other suitable communication means. Indirect communication can also be accomplished, for example, using modems with either the traditional phone system, voice over data or with cellular phones. In one example, a portable computer such as a personal data assistant may be used to transfer database information and/or infusion instructions from pharmacy system 34 to patient care device 12. The various possible means of direct and indirect communication allow information to be continuously or periodically transferred between the patient care device and other systems in network 10 (e.g. pharmacy system 34, unit station server 46, laboratory 42, etc.).

Referring again to FIG. 1, regardless of how patient care device 12 connects to or otherwise communicates with network 10, a feature of the present invention is that information is transferred, at least occasionally, between the various departments and systems within network 10 such that functionality of patient care device 12 is altered by information received from the other systems. Such a distributed, coordinated care system provides for efficient utilization of assets and improved quality of patient care by maximizing integration and utility of information from various sources in the system and by limiting opportunities for human error. As discussed above, one example of how patient care device 12 may alter its personality based upon information received from other sources is selection of specific configuration database defining a particular, treatment location-specific (e.g. NICU, Pediatrics, ICU, Surgery, Oncology, etc.), operating environment for the device 12. Similarly, prescription information, patient treatment history, drug incompatibilies, etc. from Pharmacy 34 are utilized to program device 12 and minimize data entry errors.

Other communications between patient care device 12 and the various departments or units 36, 38, 40, 42, 44, 46, 48 within network 10 serve to enhance overall quality of care. For example, communication with the biomedical engineering department (Biomed 40) helps insure device 12 safety and efficacy and optimize the efficient utilization of assets. Asset location can be accomplished by querying devices about their serial number and location. As mentioned above, device 12 location can be automatically determined by the device's connection to the network or some other means of identifying itself and its location to the network. Preventative maintenance procedures and device diagnostics can be performed remotely and blindly to the user. When problems occur, diagnostic analysis of perspective device behavior can be done remotely. This information can also be collected as a quality control device on an ongoing basis. Device utilization data can be collected to optimize the distribution of devices. As product updates or maintenance procedures come due, notices could be posted on the devices's user interface indicating the pending need. Similarly utilization of resources may also be managed from Central Supply 44. They can benefit from the same effects as the biomed group. The location and use of medical devices can be monitored and optimized based upon this data.

When a patient is first admitted in the Admissions department, a variety of data relevant to the patient is entered into the hospital's information system including patient sex, size, weight, medical condition, drug allergies, etc. This information can be used by the medical device 12 to advise the user of potential problems such as adverse drug reactions, incompatible dosing regimens and unlikely drug prescriptions. These could appear as prompts to the direct care giver or as flat-out restrictions for use beyond prescribed parameters. In patient monitoring applications it might include recommended alarm limits, monitoring periodicity, etc.

A Billing department 38 may rely on information regarding utilization of the medical device, particularly the documentation of its use or the delivery of specific medications, to effect the billing to the customer. The ability to track activities independent of their actual origin offers a way of cross checking them with the resultant improvement in efficiencies.

Networked computer terminals in Unit Stations 46, such as in a nurse's station in a particular hospital unit, allow care providers to assess remotely from any location connected into the distributed coordinated care network 10, the course of care and patient vital signs. The parameters of care (flow rate, PCA parameters, dose, monitoring intervals, alarm limits, etc.) can be altered from any location in the network, with the necessary authorization. The history of device readings, infusion site monitoring and back pressure readings, as well as the infusion and revised parameters and monitoring limits, can be reviewed remotely.

By way of non-limiting example, the use of the patient care system according to the present invention is explained in greater detail below by reference to procedures for configuring patient care device 12 for providing a prescribed treatment to a patient.

Most hospitals commonly have an established formulary of medications which defines how the medications are typically dispensed. When a patient care management system according to the present invention is first installed, a hospital committee may be formed to determine how that formulary would be applied to the patient care devices 12. The configuration definitions (e.g., by hospital unit such as ICU, NICU, Pediatrics, Oncology, Surgery, etc.) are agreed upon and the drugs and typical infusion protocols are established. In addition, all outer limit, or guard rail, conditions are defined. This information is entered into a drug library editor and configuration management program such as INFUSION MANAGEMENT SYSTEM (Alaris Medical Systems, San Diego, Calif.).

When all of the definitions are complete, then a configuration can be released. Pumps at the institution are then updated by transferring the configuration databases into some or all of their pumps. Transfer of the database information typically occurs over network transmission channel 34. Alternatively, databases may be downloaded/updated using removable media, portable computers, personal data assistants, or any other appropriate means for transferring information to patient care device 12.

Assuring that the medication is being administered to the correct patient is a key element of this system. Upon entering the hospital every patient is typically issued an identification number (patient ID) and an associated wrist band. Printed on the band or located within the band is the patient ID in text form and in coded form. Various options exist for the coded ID. For example, the band could utilize a bar code, a magnetic strip, or any other means of storing coded patient identification information. The desired configuration database might also be recorded on the wrist band. For example, a child may have a band with an indicator that the pediatric configuration database is to be used.

Figure 7:
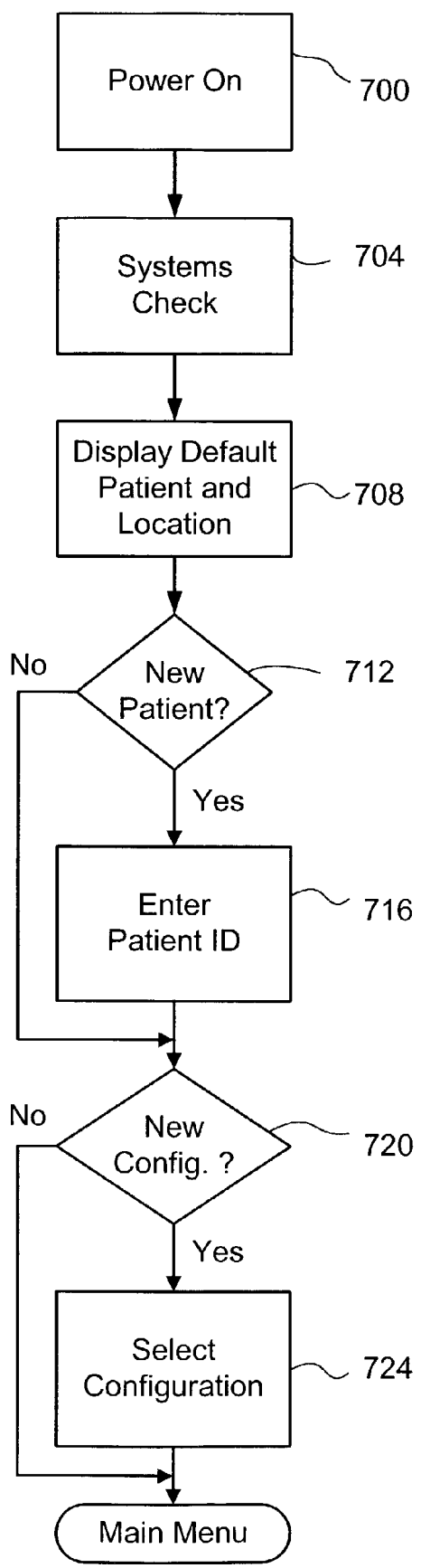
FIG. 7 illustrates the process steps used to relate a programming module with a patient, in accordance with one embodiment of the present invention.

The process steps involved in configuring a device to utilize a particular configuration database according to one embodiment of the present invention are shown in FIG. 7. After power to device 12 is turned on 700 and an internal systems check 704 is performed, the device displays on user interface 54 information pertaining to the current patient and/or the current location 708. In one embodiment of the invention, this information is recalled from the last use of the device. Alternatively, the device location and or patient identification may be determined by information received through its connection to network 10 and/or a LAN within the hospital. For example, referring to FIG. 5, a device 650 connected over LAN 620 to a server in NICU 610 receives information from the server that it should be located by Bed 1, and that a particular patient is scheduled to be in that bed. Accordingly, the device 650 utilizes that information as the default patient and location. Alternatively, device 650 automatically determines its location within the hospital by a sensor or other means of uniquely determining its location. A sensor is defined broadly herein as any device or process of sensing or detecting the location of a device, including, but not limited to, a network receptacle or port address, a network adapter, programmed location instructions, hospital records indicating location, an IR sensors or tags, RF sensors or tags, magnetic sensors or tags, or any other means of detecting the location of a device 650.

In step 712 the device queries the user whether the patient information is correct. If the patient is new to the device, or if the information is missing or incorrect, the user enters the patient ID in step 716. Patient ID is typically entered using input device 60, e.g., by scanning a patient's coded wristband including patient identification information. Alternatively, patient ID may be entered manually using a keyboard, keypad, or other interface device 54. If the current configuration database is missing or incorrect 720, the user is prompted to select the appropriate configuration database 724 (e.g. according to location, patient, physician, etc.). Alternatively, the appropriate configuration database ID may scanned into the system from the patient's identification band, or may be automatically retrieved from memory or from another location in network 10 once the patient identity, location or other patient-specific information is entered into device 12.

When a physician orders an IV, the order is typically first sent to the pharmacy (where it is entered into the hospital's pharmacy system 34). Most hospitals include a pharmacy computer system capable of maintaining records of medications already given as well as those prescribed in the future. Most commercially available pharmacy systems allow for adverse drug interactions to be checked for as part of the process prescription entering/drug dispensing process.

According to a preferred embodiment of the present invention, after the order is entered the prescription is prepared. If the drug is compounded or sourced in the pharmacy, then the prescribed medication is prepared and placed in a container. Pharmacy system 34 would then translate the infusion order from the hospital pharmacy software onto a label with encoded message and accompanying text. The label preferably includes at least the following information: patient ID, infusion protocol reference, infusion protocol deviations, or deltas, if any, and scheduled time of infusion. The label is affixed to the medication container before the prescription is transported to the unit nursing station. Medications are preferably transported from the Pharmacy to the nurse's station by hospital personnel or contained within drug dispensing cabinets near the nurse's station. Alternatively, drugs may be transported using a robotic system, such as a PYXIS system (Pyxis Corporation, San Diego, Calif.). If the drug is to be distributed from a unit nursing station, then the same type of label may be printed at the station and affixed to the drug container.

At an appropriate time, the labeled medication container is then taken to the patient's location. The bar code reader (or other data input device) is used to scan the coded drug label, the patient's coded ID band and the caregiver's ID badge, and optionally supplementary prescription information or medical device configuration instructions (including configuration database ID) printed on the label or an accompanying order. The scanned information is stored in memory 58, while device 12 first compares the scanned data to ensure that the patient identity corresponds to the patient information on the medication label, and that the prescription is being administered at the appropriate time. After the correct patient, prescription and time are verified, device 12 recalls from the active configuration database the protocol or other program information identified on the container label. The default parameter values are adjusted by any delta information included in the prescription. The user is prompted to enter, using a touch pad, bar code reader, or any other appropriate means, any missing or incomplete data. Optionally, some data may be obtained automatically from network 10 or from the appropriate department server based upon the entered patient ID, caregiver ID, user commands, etc. Once all required settings have been entered, central unit 14 displays the values, either serially or in one or more groups, to the user for verification. Once all information is entered and verified, interface unit programs the functional module(s) to perform the prescribed treatment.

It should be noted that the prescription label or other treatment instructions may identify multiple protocols and other instructions. The multiple protocols (or a single complex protocol), may define a plurality of operations to be performed by device 12. For example, the prescription label or prescription order could identify a multichannel coordinated infusion protocol involving multiple channels and infusion solutions. Additionally, the same order may identify a protocol for (or detail instructions for) programming a functional module or auxiliary device to monitor the patient physiological parameters, such as a blood pressure, heart rate, O2 saturation, respiratory rate, etc. Interface unit 14 monitors the measured parameters and, depending upon active rule sets and other configuration instructions, can modify infusion parameters based upon signals received from the physiological monitors. Such feedback systems may be useful for titration of drugs, to control anesthesia, or to regulate blood pressure.

Various embodiments of the invention have been described. The descriptions are intended to be illustrative, not limitative. Thus, it will be apparent to those skilled in the art that modifications may be made to the invention as described without departing from scope of the claims set out below.

What is claimed is:

1. A patient care system comprising:
 a patient care device including a memory for storing a plurality of configuration databases, each of said configuration databases comprising a plurality of device operating parameters;
 a network communicating with said device, said network including at least one database comprising patient-specific information; and
 means for activating a configuration database from said plurality of configuration databases based at least in part on said patient-specific information communicated to the care device, wherein the patient care device operates in accordance with at least one of said plurality of groups of operating parameters of the activated configuration database.

2. The system of claim 1, wherein said network comprises a plurality of separate databases communicating via manual interaction.

3. The system of claim 1, wherein said network comprises a plurality of separate databases communicating via automated interaction.

4. The system of claim 1, wherein communication between the network and care device is provided by a coded data input device or a network connection.

5. The system of claim 1, wherein the patient-specific information comprises any of a patient identifier, a patient location, a patient care device location, patient age, a physical characteristic or a medical characteristic.

6. The system of claim 1, wherein the activating means comprises:
  a processor within said patient care device;
  a patient-specific information input device in communication with said processor; and
  a computer program stored in said memory, said computer program executable by said processor and including instructions for activating the specific configuration database from said plurality of configuration databases based at least in part on input patient-specific information.

7. The system of claim 6, wherein the patient-specific information comprises a patient identifier, patient location, patient care device location, patient age, a physical characteristic, a physiological characteristic, a psychological characteristic, patient medical history, a patient medical record, a patient diagnosis, or a care provider identifier.

8. The system of claim 6, wherein said input device is a coded data input device or a network connection.

9. The system of claim 1, wherein said selecting means comprises a patient care device location sensor, such that selection of the specific configuration database is based, at least in part, on a location of the patient care device.

10. The system of claim 1, wherein the operating parameters within at least one of said plurality of configuration databases are organized into a plurality of groups.

11. The system of claim 10, wherein at least one of said plurality of groups is a protocol defining parameters for operating said patient care device to deliver a substance to the patient.

12. The system of claim 1, wherein at least one of said configuration databases comprises a plurality of drug delivery protocols, at least one of said protocols including a protocol identifier and at least one default parameter value for programming the patient care device to deliver a drug.

13. The system of claim 12, further comprising:
  a coded data input device operatively connected to said patient care device; and
  a drug container having a label comprising coded patient care instructions,
wherein the data input device is capable of reading the coded patient care instructions from the label into said patient care device.

14. The system of claim 13, wherein the coded patient care instructions comprise the protocol identifier, such that reading the coded patient care instructions activates the protocol identified by the protocol identifier.

15. The system of claim 14, wherein the coded patient care instructions further comprise a deviation from the default parameter, such that the patient care device is programmed to deliver the drug in accordance with the deviated parameter.

16. The system of claim 1, wherein the patient care device comprises any of an infusion pump, a syringe pump, a patient-controlled analgesia pump, an epidural pump, an enteral pump or a physiological monitor.

17. The system of claim 1, wherein the patient care device comprises an interface unit and at least one functional unit detachably and operatively connected to the interface unit, wherein the interface unit includes said memory and said functional unit provides care to the patient in accordance with said at least one of said plurality of configuration databases.

18. The system of claim 17, wherein the functional unit comprises any of an infusion pump, a syringe pump, a patient-controlled analgesia pump, an epidural pump, an enteral pump or a physiological monitor.

* * * * *